US00PP08741P

United States Patent [19]

Warriner, deceased

[11] Patent Number: Plant 8,741

[45] Date of Patent: May 24, 1994

[54] CLIMBING ROSE PLANT NAMED 'JACSAT'

[75] Inventor: William A. Warriner, deceased, late of Tustin, Calif., by Alene Beatrice Warriner, legal representative

[73] Assignee: Bear Creek Gardens, Inc., Medford, Oreg.

[21] Appl. No.: 23,883

[22] Filed: Feb. 17, 1993

[51] Int. Cl.[5] ..... A01H 5/00

[52] U.S. Cl. ..... Plt./6

[58] Field of Search ..... Plt. 6, 28

*Primary Examiner*—Howard J. Locker

*Attorney, Agent, or Firm*—Klarquist, Sparkman, Campbell, Leigh and Whinston

[57] ABSTRACT

A climber rose having a vigorous climbing habit; dark green, glossy, disease-resistant foliage; bright red flowers; repeat bloom; and the ability to bloom on new wood.

1 Drawing Sheet

The present invention relates to a new and distinct variety of rose plant of the climber class which was originated by the inventor by crossing an unnamed seedling with the variety Sympathie.

The primary objective of this breeding was to produce a new rose variety having the climbing rose growth habit of both parents, the profuse flowering on new wood of the female parent and the excellent dark green, glossy foliage of the male parent, together with the high petal count of the female parent. The objective was substantially achieved along with other desirable improvements as evidenced by the following unique combination of characteristics which are outstanding in the new variety and which distinguish it from its parents, as well as from all other varieties:

1. Vigorous climbing habit;
2. Flowers on new wood throughout the growing season;
3. Bright red, very double flowers;
4. Dark green, glossy foliage; and
5. Resistance to powdery mildew and rust.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—Sympathie.

Classification:

*Botanical.*—Rosa hybrida.

*Commercial.*—Climber.

FLOWER

Observations made from specimens grown in a garden environment in Somis, Calif., from January 1991, through October 1992.

Blooming habit: Recurrent.

Bud:

*Size.*—1¼ inches when the petals start to unfurl.

*Form.*—Short, pointed oviod.

*Color.*—When sepals first divide, bud color is Red Group 45A. When half blown, the upper and lower sides of the petals are Red Group 45A.

*Sepals.*—Color: Green Group 138C, often with a reddish blush. Surface texture: Covered in fine hairs. There are three lightly appendaged sepals. There are two unappendaged sepals with hairy edges.

*Receptacle.*—Color: Green Group 137B. Shape: Funnel. Size: Medium. Surface: Smooth.

*Peduncle.*—Length: Short (1½-2 inches). Surface: Glandular. Color: Bronzy. Strength: Bending.

Bloom:

*Size.*—Medium. Average open size is 3½ inches.

*Borne.*—Several together. If in clusters: Rounded.

*Stems.*—Long, strong. Climbing canes are long (up to 12-16 feet). The side branches or stems are 12-18 inches and terminate in flowers.

*Form.*—When first open: High centered. Permanence: Retains its form to the end. Outer petal edges curl slightly.

*Petalage.*—Number of petals under normal conditions: 35-40.

*Color.*—The upper and reverse sides of the petals are Red Group 45A. The base of each petal is a small (¼ inch×¼ inch), Yellow Group 4D half moon at the point of attachment. The major color on the upper side is Red Group 45A.

*Variegations.*—Occasional white streak on the guard petals.

*Discoloration.*—No change in general tonality at the end of the first day or at the end of the third day.

*Fragrance.*—Slight.

Petals:

*Texture.*—Thick.

*Shape.*—Round, but petal margin undulates.

*Form.*—Tips slightly recurved; edges slightly quilled.

*Arrangement.*—Imbricated, with few petaloids in the center.

*Persistence.*—Drop off cleanly.

*Lastingness.*—On the plant: Long (6 days). As a cut flower: Not tested.

Reproductive parts:

*Anthers.*—Size: Medium. Quantity: Many. Color: Yellow. Arrangement: Regular around styles, mixed with occasional petaloids.

*Filaments.*—Color: Reddish.

*Pollen.*—Color: Gold yellow.

*Styles.*—Color: Reddish.

*Stigmas.*—Color: Greenish white.

Form: Climber.

Growth: Very vigorous, upright.

Foliage: Number of leaflets on normal mid-stem leaves: 5.

*Size.*—Medium (5 inches × 3½ inches).

*Quantity.*—Abundant.

*Color.*—New foliage: Reddish. Old foliage: Dark green, glossy (Green Group 147A).

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, serrated, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when young.*—Red.

Small prickles:

*Quantity.*—On main stalks: None. On laterals: None.

I claim:

1. A new and distinct variety of rose plant of the climber class, substantially as herein shown and described, characterized particularly as to novelty by the unique combination of its vigorous climbing habit; dark green, glossy, disease-resistant foliage; bright red flowers; repeat bloom; and ability to bloom on new wood.

* * * * *

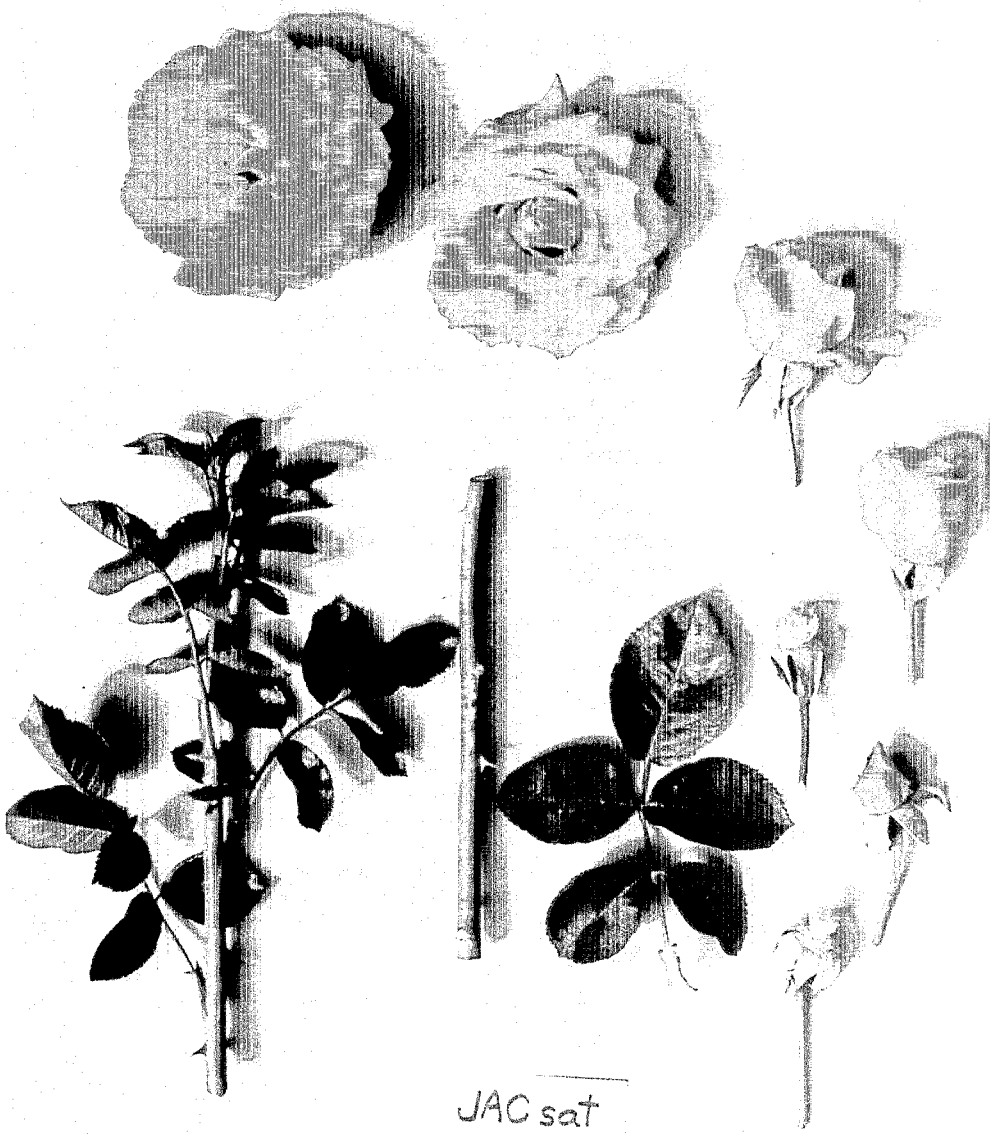
JAC sat